US012678303B2

(12) United States Patent
Kaltenborn et al.

(10) Patent No.: US 12,678,303 B2
(45) Date of Patent: Jul. 14, 2026

(54) PROSTHETIC FOOT

(71) Applicant: Ottobock SE & Co. KGaA, Duderstadt (DE)

(72) Inventors: Sven Kaltenborn, Duderstadt (DE); Martin Pusch, Duderstadt (DE); Georg Gehrmann, Göttingen (DE)

(73) Assignee: Ottobock SE & Co. KGaA, Duderstadt (DE)

( * ) Notice: Subject to any disclaimer, the term of this patent is extended or adjusted under 35 U.S.C. 154(b) by 613 days.

(21) Appl. No.: 18/006,309

(22) PCT Filed: Jul. 21, 2021

(86) PCT No.: PCT/EP2021/070383
§ 371 (c)(1),
(2) Date: Jan. 20, 2023

(87) PCT Pub. No.: WO2022/018134
PCT Pub. Date: Jan. 27, 2022

(65) Prior Publication Data
US 2023/0293318 A1 Sep. 21, 2023

(30) Foreign Application Priority Data
Jul. 21, 2020 (DE) .................... 10 2020 119 175.8

(51) Int. Cl.
*A61F 2/66* (2006.01)
*A61F 2/74* (2006.01)
*A61F 2/50* (2006.01)

(52) U.S. Cl.
CPC .................. *A61F 2/66* (2013.01); *A61F 2/74* (2021.08); *A61F 2002/5007* (2013.01); *A61F 2002/6614* (2013.01)

(58) Field of Classification Search
CPC ......................... A61F 2002/6607; A61F 2/66
See application file for complete search history.

(56) References Cited

U.S. PATENT DOCUMENTS

| | | | | |
|---|---|---|---|---|
| 809,875 | A * | 1/1906 | Wilkins | A61F 2/70 623/24 |
| 6,007,582 | A * | 12/1999 | May | A61F 2/70 623/56 |
| 2005/0071018 | A1 * | 3/2005 | Phillips | A61F 2/66 623/55 |
| 2007/0061016 | A1 * | 3/2007 | Kuo | A61F 2/70 623/24 |
| 2018/0353309 | A1 | 12/2018 | Schlafly | |

FOREIGN PATENT DOCUMENTS

| | | |
|---|---|---|
| DE | 102008008281 A1 | 8/2009 |
| WO | 2018166905 A1 | 9/2018 |

* cited by examiner

*Primary Examiner* — Bruce E Snow
(74) *Attorney, Agent, or Firm* — WCF IP

(57) ABSTRACT

The invention relates to a prosthetic foot comprising a main body (10), a proximal connection device (15) for connecting the prosthetic foot (1) to a further prosthesis component, and a foot-front component (12) which is pivotally mounted on the main body (10) and which is associated with a resistance device (20), which resistance device retards plantar flexion of the foot-front component (12), wherein the foot-front component (12) is mounted on the main body (10) via at least one resilient component (30, 31, 32) which moves the foot-front component (12) back into a starting position after a deflection.

16 Claims, 4 Drawing Sheets

PROSTHETIC FOOT

Figure 1:
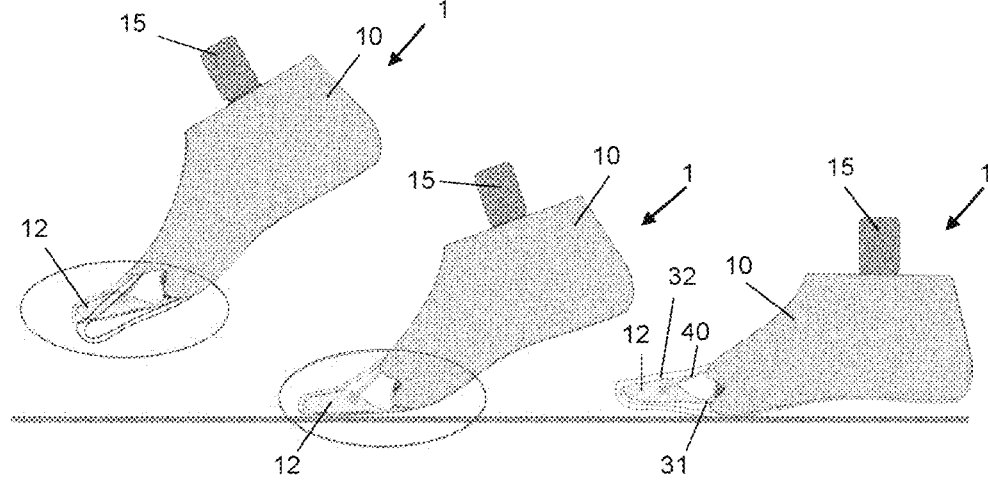

The invention relates to a prosthetic foot having a main body, a proximal attachment device for connecting the prosthetic foot to a further prosthetic component and having a forefoot component which is mounted pivotably on the main body and which is assigned a resistance device which retards plantar flexion of the forefoot component.

Prosthetic feet or prosthetic feet inserts form the distal termination of a prosthetic fixture and are generally worn in a shoe. An important task of a prosthetic foot is to provide sufficient stability for the prosthetic foot user during standing and walking and to introduce forces into the ground. Prosthetic feet can be designed in very different ways in order to provide a pleasant gait behavior. Modern feet frequently have spring elements which mitigate the heel strike, permit a pleasant rolling movement and, furthermore, provide sufficient stability in order, at the end of the stance phase, to provide a forward impulse for the patient even in the forefoot region. The rolling characteristics differ from prosthetic foot to prosthetic foot. In the case of a rigid prosthetic foot having a substantially horizontal forefoot section, the prosthetic foot tilts or rotates over the frontmost tip, as a result of which the effective foot length is maximized. However, the rolling behavior is unnatural and requires considerable expenditure of energy. In order to improve the rolling behavior, the forefoot regions are formed with a curvature, similarly to the natural foot curvature, as a result of which the force introduction point migrates forward during the rolling process. If spring elements are arranged or formed on the foot, they contribute to changing the rolling behavior.

A problem with rigid prosthetic feet is that there is the risk that, during the swing-through, the foot tip drags or gets caught on the ground. This may result in the prosthesis user stumbling. In order to avoid this, the prosthetic is sometimes made shorter, which leads to back injuries. Alternatively or additionally, the prosthesis user may unnaturally lift the knee during walking or execute circumduction. Such compensating movements increase the energy required for walking and may lead to unintentional loadings of the rest of the locomotion apparatus.

DE 10 2008 008 281 A1 discloses a prosthetic foot insert having a main body and a forefoot component which is mounted in an articulated manner about a pivot axis and is coupled to a hydraulic damper in order to change the pivoting movement relative to the main body on the basis of sensor signals. On the basis of an inclination angle or an absolute angle, for example, the flow resistance within the hydraulic damper can be adjusted. A spring restores the forefoot component into a neutral position. As a result, depending on the position of the prosthetic foot, it is possible to retard plantar flexion of the forefoot component, and therefore an easy swing-through with a dorsiflexed forefoot component is possible. The design is comparatively complicated and requires a large number of moveable components.

It is the object of the present invention to provide a prosthetic foot which is constructed simply and with which as natural and safe a gait behavior as possible can be achieved and the potential for stumbling significantly reduced.

According to the invention, this object is achieved by a prosthetic foot having the features of the main claim. Advantageous refinements and developments of the invention are disclosed in the dependent claims, the description and the figures.

The prosthetic foot having a main body, a proximal attachment device for connecting the prosthetic foot to a further prosthetic component and having a forefoot component which is mounted pivotably on the main body which is assigned a resistance device which retards plantar flexion of the forefoot component envisages that the forefoot component is mounted on the main body via at least one elastic component which moves the forefoot component back into a starting position after a deflection. While a separate resetting spring is required in the prior art in order to move the forefoot component back into the neutral position counter to a resistance force by the hydraulic damper in the plantar direction, according to the invention the forefoot component is moved back into the starting position via the elastic component, which at the same time forms a bearing. As a result, it is not necessary to provide a rigid axle with a separate damper and a separate resetting spring; on the contrary, the resetting movement after the dorsiflexion at the end of the stance phase is brought about by the elastic component. After the toe-off and at the beginning of the swing phase, a maximum dorsiflexion of the forefoot component is present. This will also be retained for part of the swing phase. At least the plantar flexion movement is retarded by the resistance device until the prosthetic foot has passed the foot located on the ground in the walking direction. The fact that the forefoot component is raised in the dorsal direction means that the knee does not have to be unusually raised in order to provide sufficient ground clearance so that the swing-through can easily take place. Circumduction is just as little necessary.

A development of the invention makes provision that the elastic component is designed as a leaf spring, an elastomeric element or as a prosthetic foot cosmetic. The configuration of the elastic component as a leaf spring, which can be designed as a separate component or as part of the forefoot component, permits simple fastening via, for example, screws or other mechanical fastening components such that the forefoot component can be mounted in a form-fitting and force-transmitting manner via the elastic component. The leaf spring is formed elastically from a dimensionally stable material, for example a fiber composite material or a metal. Alternatively, the forefoot component can be fastened to the main body via an elastomeric element, the forefoot component can be embedded in the elastomeric element, or the elastomeric element can be clamped, screwed, adhesively bonded, welded or cast or integrally formed or fastened in some other way to the forefoot component. The elastic component can likewise be designed as a prosthetic foot cosmetic which encases the main body together with the forefoot component in order to provide as natural an appearance as possible for the prosthetic foot. The prosthetic cosmetic may have the outer form of a natural foot and form a cavity for receiving the prosthetic foot insert with the main body and forefoot component. In addition to mounting the forefoot component just via the prosthetic foot cosmetic, it is possible that the prosthetic foot cosmetic, which is formed from an elastic material or has elastic sections, contributes, in addition to the leaf spring or the separate elastomeric element, to resetting the forefoot component into the starting position after a dorsal deflection.

A development of the invention makes provision that the resistance device has an actuator, in particular a hydraulic or pneumatic damper, a friction element, a blocking device, a drive and/or a magnetic brake, in order to delay the resetting movement on the basis of the resetting forces of the elastic component as desired. In particular in the case of non-driven prosthetic feet, the resistance device has an actuator which is controlled without electric sensors. The control preferably takes place via a mechanical timing element which particularly preferably is adjustable. Particularly preferably, the resistance device is designed as a passive fluid damper which manages without electronic components. A resistance device without sensor-controlled actuators can also be used in the case of prosthetic feet having a drive. The drive is designed in particular as a motor which can be driven counter to the resetting movement of the forefoot component into its starting position in order to delay the resetting or to prevent it for a required period of time. Alternatively, a short-circuiting circuit can delay or prevent movement of the forefoot component. By means of corresponding activation or switching of the drive, in particular electric motor, the resistance against a resetting movement can be reduced or eliminated such that the resetting can be undertaken by means of the elastomeric component.

Advantageously, the forefoot component has a length of 15% to 35% of the overall length of the prosthetic foot, as a result of which a rolling behavior approximate to the rolling behavior of a natural foot can be set.

The resistance device can have a locking device which is assigned a deactivation device. The movement of the forefoot component relative to the main body can be blocked via the locking device such that there is no flexibility during the rolling movement. This provides increased stability for the prosthetic foot user since maximum control of the force introduction behavior is obtained. The lock can be removed via the deactivation device. If the resistance device is designed, for example, as a hydraulic or pneumatic damper, the locking device is a valve or a switchable throttle which blocks a corresponding movement of a piston. The deactivation device opens the valve or the throttle and is, for example, a motor or another actuator. In the case of a magnetic brake, for example on the basis of magneto-rheological fluids or a similar device, application of a magnetic field via a solenoid achieves a corresponding increase in viscosity or generates a magnetic field which blocks a relative movement. Switching off the magnetic field then switches the resistance device into a normal operating mode, i.e. deactivates the locking device. If the resistance device is a friction element, in addition to a form-fitting lock, a relative movement can be prevented, for example, by pressing two friction disks or other friction elements against one another. The form-fitting element can be brought from an engagement position into a disengaged position by an actuator, a spring or the like.

The deactivation device can be designed so as to be able to be triggered depending on a spatial position, an angular position, an acceleration, a movement speed, the time and/or an action of force or torque on the prosthetic foot. The characteristic values of the spatial position, the angular position, the acceleration, the movement speed, the time and/or an action of force are determined via corresponding sensors or derived from the sensor values. The control device for controlling the deactivation device, the locking device and/or the resistance device processes the sensor data by means of a processor. For this purpose, the deactivation device can be assigned at least one acceleration sensor, an angle sensor, a gravitation sensor, a force sensor, a torque sensor, an IMU (inertial measurement unit) and/or a timing element, or there can be coupling via a control device. On the basis of the corresponding sensor values either of the main body and/or of the forefoot component, the resistance device can then be activated and deactivated.

Advantageously, the resistance device is designed to be effective in the swing phase from the beginning of the swing phase as far as the middle swing phase in order to keep the forefoot component dorsally flexed.

The resistance device can be coupled to the forefoot component via a rod transmitting compressive forces. As a result, it is possible to couple the resistance device effectively to the resistance device both in the traction direction and in the compression direction and to position the resistance device at or in the main body away from the forefoot component. Alternatively or additionally, a coupling transmitting torque can be provided between the forefoot component and the resistance device in order to connect the resistance device to the forefoot component and to transmit forces and/or torques. The coupling transmitting torque can be designed, for example, as a freewheel or ratchet mechanism which is coupled to the resistance device and permits dorsiflexion of the forefoot component without substantial resistance, but blocks the resetting movement or provides it with a resistance. The blocking effect is eliminated at the desired time or in the desired state.

The resistance device can also be coupled to the forefoot component via a flexible traction element which is relaxed in the event of dorsiflexion of the forefoot part. In the embodiment as a flexible traction element, the force transmission device is designed, for example, as a band, as a cable or a chain and is relaxed in the event of a forefoot load or flexion in the dorsal direction. The resistance device can be pretensioned, for example, via a spring or another force accumulator so that the traction element is pretensioned. The pretensioning of the traction element acts in the dorsiflexion direction. For this purpose, the resistance device is slightly pretensioned by a spring acting in the dorsiflexion direction or by another force accumulator and can be moved in the pretensioning direction by said pretensioning force such that the traction element, which is partially relaxed by pivoting of the forefoot component, permits the resistance device to be retracted by means of the force accumulator. The elastic component acts counter to said pretensioning force, and therefore the forefoot component is held in the starting position in an unloaded state. In the event of a corresponding pivoting of the forefoot component, the traction element is relaxed, the force accumulator or the spring relaxes and the resistance device or a component coupled thereto is moved. If, in an alternative refinement, the dorsiflexing force on the forefoot component ceases, the traction on the traction element exceeds the pretensioning force of the traction element and the resistance device extends as soon as the resistance thereof is lowered from a high to a low value. The resistance device extends with a delay if the damper unit of the resistance device does not permit a rapid extension.

Advantageously, the forefoot component is formed from a dimensionally stable material, in particular a plastic, a fiber composite material or a light metal alloy, in order to provide sufficient forefoot stability, in particular when the resistance device is locked. The forefoot component can also be produced from an elastomer, preferably from the same elastomer as the elastomeric element. The forefoot component and the elastomeric element can be formed integrally. This is appropriate in particular if the forefoot component does not have any further functional properties and in particular does not have to transmit relatively great forces, but rather is intended to provide only a visual compensation if the forefoot length is lacking.

The forefoot component can be adhesively bonded in the prosthetic cosmetic, in particular if the prosthetic cosmetic provides the elastic component, in order to bring about a resetting into the starting position after the deflection at the end of the stance phase.

The forefoot component can be installed in addition to further foot functions and used independently thereof. For example, it is used in addition to a hydraulic ankle, heel height adaptation, a driven ankle unit and the like. Should there not be any space in the region of the ankle or of the adapter unit because of the functional uses, the resistance device, locking device and/or the deactivation device and other required components may also be attached or used in other regions of the foot prosthetic. For example, on or between springs, in particular leaf springs, if the components do not negatively affect the deformation of the springs.

Figure 2:
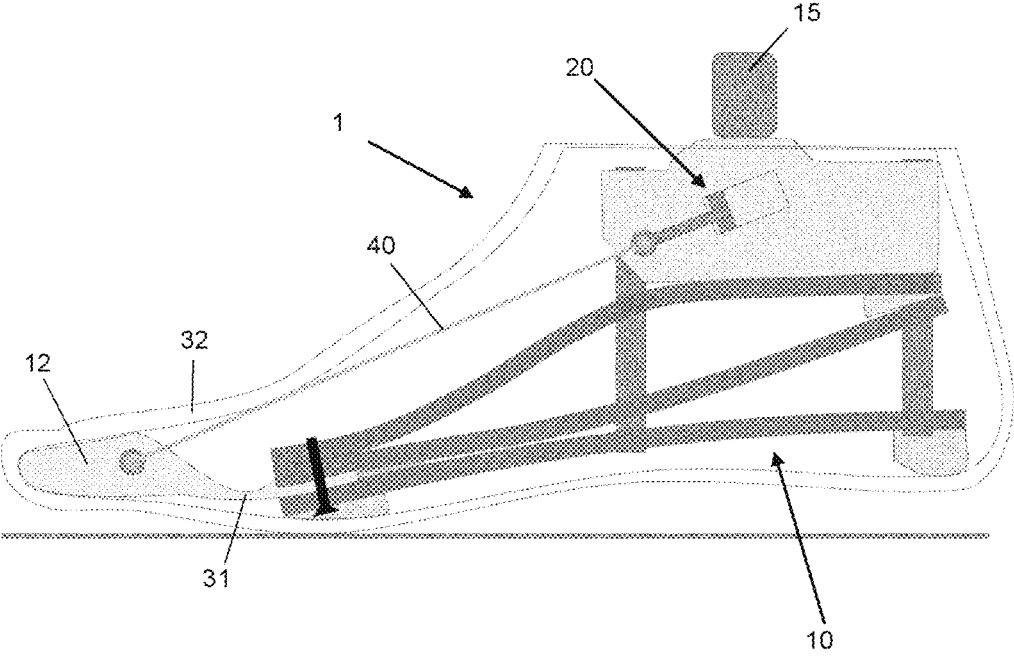
Figure 3:
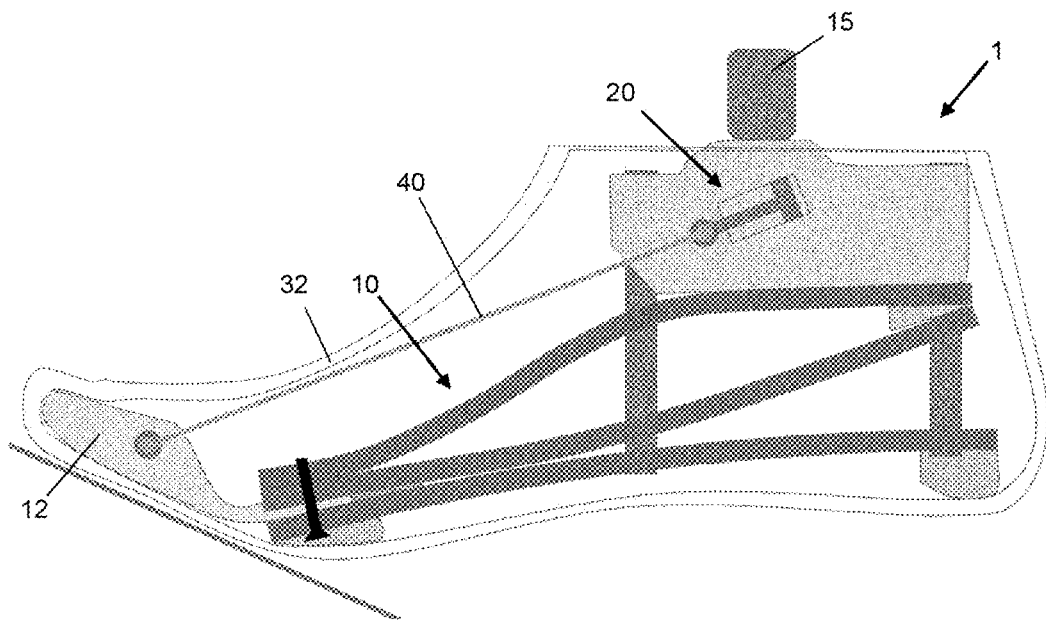
Figure 4:
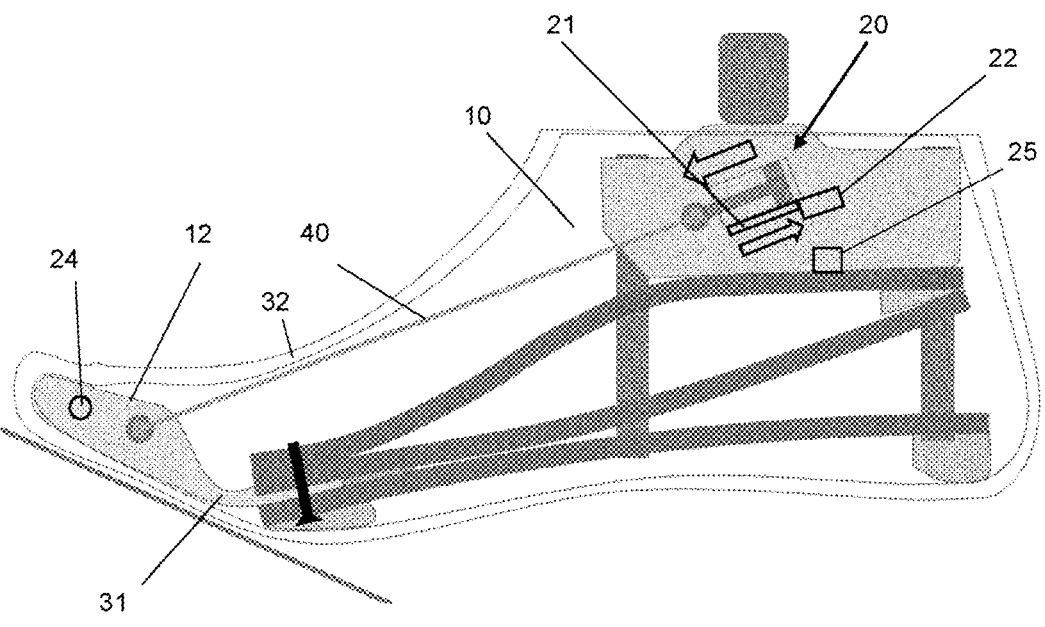
Figure 5:
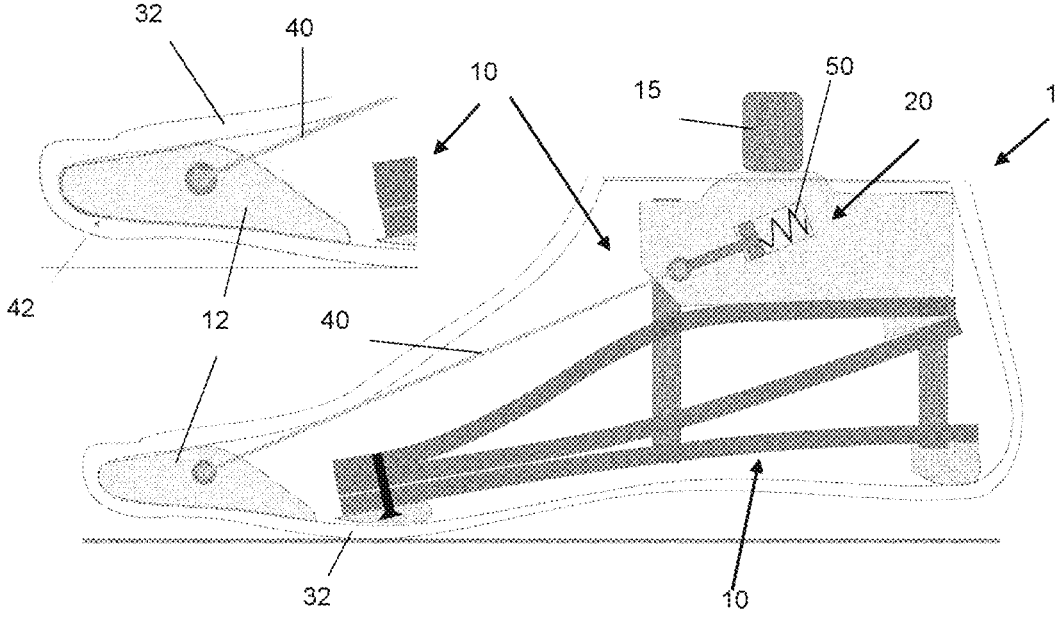
Figure 6:
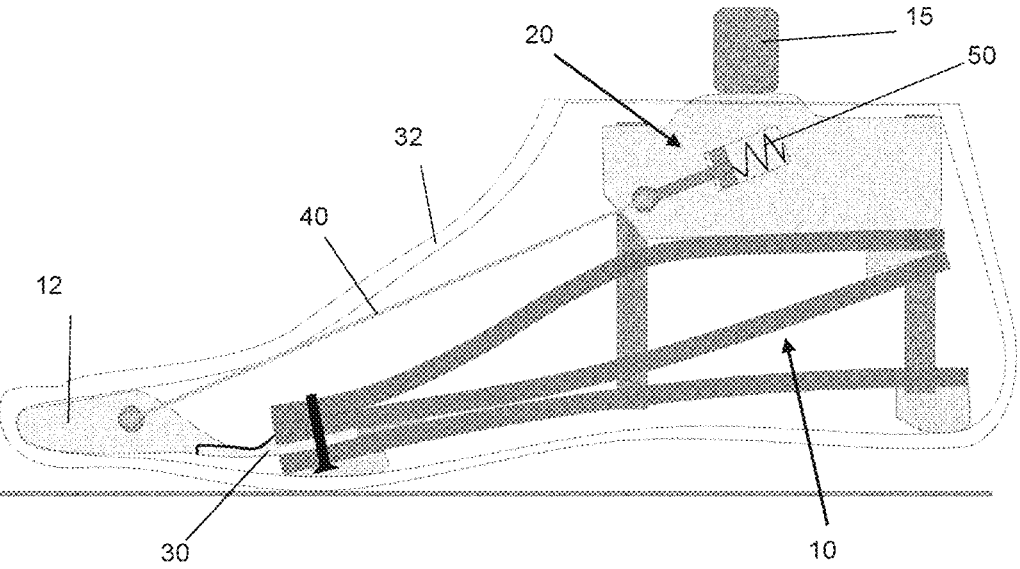
Figure 7:
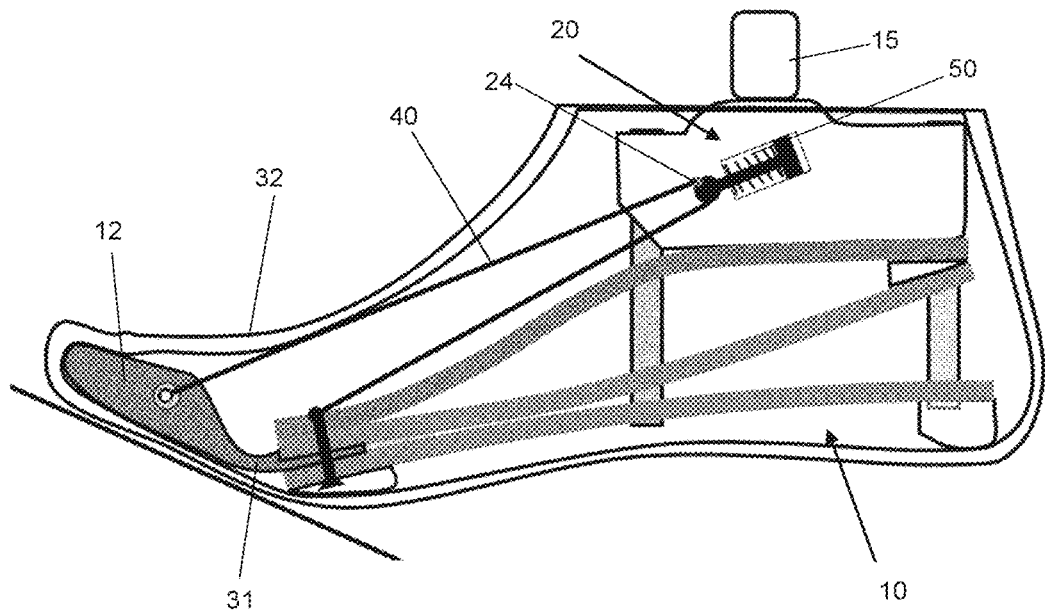

Exemplary embodiments of the invention will be explained in more detail below with reference to the attached figures, in which:

FIG. 1—shows the movement sequence of a prosthetic foot at the end of the stance phase and at the beginning of the swing phase;

FIG. 2—shows a schematic sectional illustration of a first embodiment of a prosthetic foot;

FIG. 3—shows an illustration of the prosthetic foot according to FIG. 2 at the end of a stance phase;

FIG. 4—shows a variant of FIG. 3 with sensors;

FIG. 5—shows a variant of the invention with the configuration of the elastic component as a prosthetic cosmetic;

FIG. 6—shows a variant of FIG. 2 with a separately formed elastic component; and FIG. 7 shows a variant of the invention with a force transmission device with a spring element and a deflecting pulley.

FIG. 1 shows the movement sequence at the end of the stance phase with reference to three images depicting the states. The right illustration shows a prosthetic foot 1 having a main body 10, at the upper proximal end of which an attachment device 15 is arranged in order to be able to fasten the prosthetic foot 1, for example, to a lower leg tube or a lower leg socket. The proximal attachment device 15 can differ in shape. A conventional manner of attaching a prosthetic foot 1 to a proximal prosthetic component consists in a pyramid adapter via which, in addition to form-fitting securing, the prosthetic foot 1 can also be aligned relative to the proximal prosthetic component. The proximal prosthetic component can also be designed as a prosthetic ankle joint.

A forefoot component 12 which has the function of the toes of a natural foot is arranged at the front distal end of the main body 10. The forefoot component 12 is dimensionally stable in its distal end region and is not provided to deform under load. A force transmission device 40, for example in the form of a rod or a flexible, in particular inelastic traction means, such as a strap, cable, chain or band, leads from the forefoot component 12 to a resistance device 20, not illustrated, which is arranged at or within the main body. The main body 10 together with the forefoot component 12 and the force transmission device 40 is encased by a prosthetic cosmetic 32 which can have an outer shape approximate to the natural appearance of a foot. The prosthetic cosmetic 32 is flexible and optionally elastic. In the right illustration of FIG. 1, the prosthetic foot 1 is in a middle stance phase, in which a first rolling movement can already be seen since the heel has already been raised somewhat. The forefoot component 12 is not yet in contact with the ground. In the exemplary embodiment illustrated in FIG. 1, the connection between the main body 10 and the forefoot component 12 is produced via an elastomeric element 31 which surrounds the forefoot component 12 or is secured or formed thereon. The elastomeric element 31 forms an elastic component such that the forefoot component 12 is movable relative to the main body 10. The elastic component 31 forms, for example, a film hinge, with the dimensioning of the elastic component being of such a size that the forces occurring during normal operation under normal use of the prosthetic foot 1 can be absorbed.

In the middle illustration of FIG. 1, the prosthetic foot is in the region of the terminal stance phase with forefoot loading. The heel has already been raised to a great extent and the forefoot component 12 rests on the ground. The main body 10 is tilted relative to the starting position, which is shown in the right illustration of FIG. 1, with respect to the support region of the forefoot component 12; that is to say, dorsiflexion of the forefoot component 12 has taken place. This is understood as meaning that the forefoot component 12 is pivoted about a pivot axis in the direction of the dorsum of the foot or instep. A movement of the forefoot component 12 downward in the direction of the ground is called plantar flexion. By means of the dorsiflexion of the forefoot component 12, the force transmission device 40 has been moved or relaxed, thus resulting in a movement of the front end of the force transmission device in the direction of the resistance device, not illustrated, or the proximal attachment means 15.

In the left illustration of FIG. 1, the prosthetic foot 1 is in the swing phase, and the main body 10 and the forefoot component 12 no longer have any contact with the ground. It can be seen in the left illustration in FIG. 1 that the forefoot component 12 is furthermore in a dorsiflexed position relative to the main body 10. The starting position, as is shown in the right illustration of FIG. 1, is indicated by the contour line. Said dorsiflexed position is maintained for a certain period of time or for a certain movement situation within the swing phase, namely at least until the prosthetic foot 1 has passed the other, contralateral foot. The dorsiflexed position of the forefoot component 12 shortens the effective foot length of the prosthetic foot insert or prosthetic foot 1, as a result of which, during the swing-through of the prosthetic foot 1 during the stance phase, the knee does not have to be raised to an unusually high degree. This prevents compensating movements and also reduces the risk of stumbling.

The forefoot component 12 is a separate part of the prosthetic foot and is secured to the main body 10 or assigned permanently thereto during the use of the prosthetic foot 1. The length of the forefoot component can vary and is between 15% and 35% of the overall length of the prosthetic foot 1. Different foot sizes or shoe sizes can be reproduced via the forefoot component 12 without the main body 10, which may have a complex mechanical design, having to be changed.

FIG. 2 shows, in a schematic sectional illustration, a prosthetic foot 1 having a main body 10 which has a complex mechanical design with a plurality of leaf spring components which are secured on one another via spacer elements and damper components and travel limiting devices. The proximal attachment device 15 is arranged on a support which serves at the same time as a receptacle for the resistance device 20. The leaf spring components are secured on the support. In the exemplary embodiment illustrated, the resistance device 20 is designed as a hydraulic damper device which is coupled to the forefoot component 12 via a compression rod 40. The forefoot component 12 has a front section on which the bearing point of the force transmission device 40 is arranged. A rear section facing the main body 10 is fastened in a form-fitting manner to the main body 10 via a screw connection and is clamped between two leaf spring components. The elastic component 31 is formed at the transition between the clamped rear section and the front section of the forefoot component 12, the elastic component ensuring that the forefoot component 12 is held in a starting position, with a deflection in the dorsal direction being able to take place when a sufficiently large force or a sufficiently large torque is applied. A deflection in the plantar flexion direction is prevented or at least made difficult by the force transmission device 40. At the end of the stance phase, the prosthetic foot 1 is rolled via the forefoot, as a result of which dorsiflexion of the forefoot component 12 occurs. The elastic component 31 which is designed as an integral part of the forefoot component 12 is deformed and the dorsiflexion takes place counter to the resetting force provided by the elastic component 31.

The situation of dorsiflexion of the forefoot component 12 is illustrated in FIG. 3. The forefoot component 12 is bent in the direction of the dorsum of the foot, i.e. upward. The force transmission device 40 displaces the piston of the resistance device 20 to the rear, with the resistance of the displacement movement of the hydraulic piston being able to be adjusted within the resistance device 20. The rolling behavior of the prosthetic foot can be changed via the adjustable resistance. If the force transmission device 40 is able to transmit only small compressive forces if any at all, a movement of the hydraulic piston within the resistance device can be brought about or assisted by a spring force or another energy accumulator. In addition to the configuration of the resistance device 20 as a hydraulic damper, it can also be designed as a pneumatic damper, another fluid damper, a friction brake or else on the basis of magneto-rheological effects.

FIG. 4 shows a variant of the design from FIG. 3, in which a plurality of sensors 24, 25 are arranged on the prosthetic foot. For example, an acceleration sensor 24 is arranged on the forefoot component 12 and an IMU 25 or a spatial position sensor on the support, with further sensors being able to be arranged on the prosthetic foot. For example, force sensors, time switching elements, angle sensors or other sensors can be arranged at different points of the prosthetic foot in order to sense desired or required data. A control device as part of a deactivation device 22 is arranged on the support. The control device has the necessary components for data processing; in particular, it has a memory, processors, optionally amplifiers and at least one connection to an energy accumulator in order to be able to ensure sufficient data processing. The deactivation device 22 serves to deactivate or to activate a locking device 21, which is illustrated schematically. For this purpose, actuators, not illustrated, for example electric motors, relays, switching elements, magnetic fields or the like are used. Equally, valves can be set or other resistances changed via the control device, and therefore the resistance device 20 means that there is a lower resistance for the retraction movement or the dorsiflexion of the forefoot component 12 than for the plantar flexion movement. This is indicated by the arrows of differing thickness. The locking device can block the plantar flexion; equally, the resistance can be changed in the respective direction of movement at certain points in time or in certain situations via the same components.

It can be gathered from FIGS. 2 to 4 that the sole of the foot or the prosthetic cosmetic 32 forms a cavity in which the individual components of the prosthetic foot are inserted. The prosthetic cosmetic 32 is advantageously likewise elastic and, together with the elastic component of the forefoot component 12, brings about a resetting movement into the starting position according to FIG. 2. The resetting movement following dorsiflexion is retarded via the resistance device 20 or prevented until a point in time at which swinging-through has taken place. The locking device 21 can then be deactivated via the control device and the deactivation device 22 and a plantar flexion of the forefoot component 12 permitted. The locking device 21 can also completely block the resistance device 20 such that dorsiflexion is not possible. This is advantageous, for example, in a special situation or in situations in which maximum stability when standing is desired. For this purpose, a corresponding signal can be sent to the control device and to the locking device 21 via an external interface.

Both the force transmission device 40 and the resistance device 20 can be arranged retrospectively on already existing prosthetic foot components, and therefore retrofitting of a flexible forefoot component can easily be permitted. If there are no elastic components for providing a resetting force, they can likewise be retrofitted.

FIG. 5 shows illustrations of a variant of the invention, in which the dimensionally stable forefoot component 12 is coupled solely as an elastic component to the rest of the main body 10 via the prosthetic cosmetic 32. For this purpose, the forefoot component 12 is adhesively bonded within the prosthetic component 32 via an adhesive layer 42. Alternatively, the front region of the prosthetic cosmetic 32 can also be cast and can form a dimensionally stable bearing for the force transmission device 40. A clearance can be seen between the front end of the main body 10 and the rear end of the forefoot component 12. In order to achieve sufficient positional stability of the respective components, the main body 10 is advantageously likewise fixed in the prosthetic cosmetic 32, for example mounted, adhesively bonded and/or welded in a form-fitting manner. Within the resistance device 20, which is designed, for example, as a hydraulic damper, a force accumulator 50 is arranged in the form of a tension spring which pulls the piston of the hydraulic damper to the right. As a result, the force transmission device 40 is loaded in tension, and therefore it can also be designed as a flexible, flexurally slack, in particular inelastic element. This has the advantage that the force transmission device 40 can be guided virtually as desired along the main body 10, for example by deflecting elements or pulleys. As a result, the design scope is increased and the bearing points and the positioning of the resistance device 20 can be arranged in optimized form in the main body or support or on the forefoot component 12. The force accumulator 50 can also be arranged as a compression spring on the other side of the piston. In another structural configuration of the resistance device, for example with rotationally mounted components, the force accumulator can also be designed as a torsion spring or spiral spring. Pneumatic elements or elastomeric elements, disk springs or the like for pretensioning the force transmission device 40 can likewise be provided in the form of an element only transmitting tensile forces. The configuration of the force transmission device 40 as a flexible and inelastic component with a pretensioning device can also be used in all other embodiments of the elastic component.

A variant of FIG. 2 is illustrated in FIG. 6 in which a separate elastic component 30 in the form of a leaf spring provides the connection between the forefoot component 12 and the main body 10. The elastic component in the form of a leaf spring is a separate component which can be securable exchangeably both on the main body and on the forefoot component 12. The elastic component 30 can likewise be formed separately and fastened permanently to the forefoot component 12, for example welded, adhesively bonded, cast or fastened thereto in similar ways. A force accumulator 50 in the form of a spring is also arranged here in the resistance device.

Common features of all of the embodiments is that the elastic component does not form a rigid pivot axis about which the forefoot component can be pivoted relative to the main body, and at the same time the resetting movement into a starting position after the deflection takes place simultaneously via the elastic component. In addition to an unsteady pivot axis, a notch or material weakening formed similarly to a film hinge, but providing resetting forces can be provided in the elastic component. The pivot axis will therefore preferably lie in the notch or in the region of the material weakening and should therefore be virtually stationary.

FIG. 7 illustrates a variant of FIG. 6. The basic design of the prosthetic foot corresponds to that which has been described in previous FIGS. 2 to 6. The force transmission element 40, which is designed as a cable, strap or other flexible force transmission element 40, is changed. The force transmission element 40 is in particular rigid in tension and fastened at a first end to the forefoot component 12 and at the second end to the main body 10. In the exemplary embodiment illustrated, the fastening is carried out at the screw with which the three leaf springs are fastened to one another in the region of the front end of the main body 10 and via which the forefoot component 12 is fastened thereto via the elastic component 31. The force transmission device 40 is guided about a deflecting pulley 24 or a deflecting element which is fastened moveably to the resistance device 20. The movement takes place counter to a spring force of a force accumulator or a spring 50. In the exemplary embodiment illustrated, the spring 50 is arranged within the resistance device 20; alternative arrangements of the spring 50 are possible, for example outside a cylinder or the housing in which the resistance device 20 is arranged. The resistance device 20 therefore has a force accumulator 50 in the form of a spring or an elastomeric element which can move the resistance device 20 counter to its own small friction in the dorsiflexion direction of the forefoot component 12. If the forefoot component 12 is unflexed, the holding forces of the forefoot component 12 via the elastic component 31, optionally in conjunction with the elastic prosthetic cosmetic 32, are of such a magnitude that the resistance device 20 does not retract. The unflexed position is illustrated, for example, in FIG. 6. The force transmission device 40 in the form, for example, of a tension cable is slightly tensioned. During a rolling movement along the middle foot region, the ground reaction force causes the forefoot component 12 to be flexed, as is shown, for example, in FIG. 7. The force transmission device 40 is not relaxed in the process; on the contrary, the resistance device 20, or the piston within the resistance device 20, which piston is connected to the deflecting pulley 24, moves into a retracted position as shown in FIG. 7. The force transmission device 40 or the tension cable is not relaxed, but rather remains slightly tensioned. If a dorsiflexing ground reaction force then eases up, the force at the force transmission device 40 or the tension cable increases and pulls the resistance device 20 by the deflecting pulley 40 in the opposite direction, in the direction of the forefoot component 12, and tensions the spring 50 again. If the resistance force of the resistance device 20 is set to be high, the forefoot component 12 remains dorsally flexed. Depending on how the resistance device 20 is set and a resistance force or damping is opposed to a retraction movement of the piston rod, on which the deflecting pulley 24 is arranged, the forefoot component 12 drops downward and carries out plantar flexion. The spring or the force accumulator 50 has a comparatively small pretensioning force, and therefore it has only a small influence on the plantar flexion movement of the forefoot component 12.

The action of the force accumulator 50 can be controlled by positioning the coupling points of the force transmission device 40 or of the tension cable on or in the forefoot component 12. If the fastening point or coupling point on the forefoot component 12 is positioned close to the sole of the foot, the force transmission device 40 pulls in the rearward direction, if the forefoot component 12 is not dorsally flexed, into the joint formed by the elastic component 31. The elastic resetting forces of the elastic components 31, 32 hold the forefoot component 12 in the plantar-flexed position. If the coupling point of the force transmission device 40 is arranged further proximally on the forefoot component 12, i.e. in the direction of the dorsum of the foot, the pretensioning by the force accumulator 50 acts in a torque-forming manner about the joint which is formed by the elastic component 31, and the forefoot component 12 tends to carry out dorsiflexion. By means of the positioning of the coupling point on the forefoot component 12 together with the setting of the pretensioning at the force accumulator 50 in conjunction with the setting of the resistance force in the resistance device 20, essential aspects of the behavior of the prosthetic foot can be adjusted simply and without use of sensors and motorized drives. In this way, a robust and simply constructed prosthetic foot can easily be adapted to the respective user and the respective use conditions without use of external energy.

By means of the arrangement of a deflecting pulley 24 or a deflecting device for the force transmission device 40, force is distributed according to the block and tackle principle. A plurality of deflecting elements or deflecting pulleys may be present in order to produce a force-travel coupling to the force accumulator 50 and the resistance device 20.

The resistance device 20 optionally with the deflecting device 24 and the integrated force accumulator 50, can be manufactured separately and secured on the main body 10, for example on a support or a receiving device for the proximal attachment device 15. Instead of securing on the support, the resistance device 20 can be fastened to one of the leaf springs of the spring assembly of the main body 10 by the force accumulator 50, optionally also without a deflecting device 24.

The invention claimed is:

1. A prosthetic foot, comprising:
   a main body;
   a forefoot component;
   at least one elastic component;
   a proximal attachment device for connecting the prosthetic foot to a further prosthetic component and to the forefoot component,
   wherein the forefoot component is mounted pivotably on the main body; and
   a resistance device connected to the main body which retards plantar flexion of the forefoot component,
   wherein the forefoot component is mounted on the main body via the at least one elastic component which provides in combination with the resistance device a delayed movement of the forefoot component back into a starting position after a dorsiflexion deflection by acting against resistance provided by the resistance device.

2. The prosthetic foot as claimed in claim 1, wherein the at least one elastic component is designed as a leaf spring, elastomer element, or prosthetic foot cosmetic.

3. The prosthetic foot as claimed in claim 1, wherein the resistance device comprises one or more of an actuator, a friction element, a blocking device, a drive, and a magnetic brake.

4. The prosthetic foot as claimed in claim 1, wherein the forefoot component has a length of 15% to 35% of an overall length of the prosthetic foot.

5. The prosthetic foot as claimed in claim 1, wherein the resistance device has a locking device which is assigned a deactivation device.

6. The prosthetic foot as claimed in claim 5, wherein the deactivation device is designed to be triggered depending on one or more of a spatial position, an angular position, an acceleration, a movement speed, a time, and an action of force or torque on the prosthetic foot.

7. The prosthetic foot as claimed in claim 6, wherein the deactivation device comprises or is coupled to one or more of an acceleration sensor, an angle sensor, a gravitation sensor, a force sensor, a torque sensor, an IMU, and a timing element.

8. The prosthetic foot as claimed in claim 1, wherein the resistance device is designed to be effective in a swing phase at least as far as a middle swing phase.

9. The prosthetic foot as claimed in claim 1, wherein the resistance device is coupled to the forefoot component via a rod which transmits compressive forces and/or a coupling which transmits torque.

10. The prosthetic foot as claimed in claim 1, wherein the resistance device is coupled to the forefoot component via a flexible traction element which is relaxed in dorsiflexion of the forefoot component.

11. The prosthetic foot as claimed in claim 10, wherein the flexible traction element is pretensioned via the resistance device.

12. The prosthetic foot as claimed in claim 1, wherein the forefoot component is formed from a dimensionally stable material.

13. The prosthetic foot as claimed in claim 2, wherein the forefoot component is adhesively bonded in the prosthetic cosmetic.

14. The prosthetic foot of claim 3, wherein the actuator is selected from the group consisting of a hydraulic damper and a pneumatic damper.

15. The prosthetic foot of claim 1, wherein the at least one elastic element does not comprise a hinge.

16. The prosthetic foot of claim 1, wherein the at least one elastic component is a prosthetic foot cosmetic.

\* \* \* \* \*